United States Patent
Heller

(10) Patent No.: US 12,284,739 B2
(45) Date of Patent: *Apr. 22, 2025

(54) LIGHTING SYSTEMS AND APPLICATIONS THEREOF

(71) Applicant: MIDWEST LIGHTING INSTITUTE, INC., Cottage Grove, WI (US)

(72) Inventor: Rodney Heller, Cottage Grove, WI (US)

(73) Assignee: MIDWEST LIGHTING INSTITUTE, INC., Cottage Grove, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/615,542

(22) Filed: Mar. 25, 2024

(65) Prior Publication Data
US 2024/0365456 A1   Oct. 31, 2024

Related U.S. Application Data

(63) Continuation of application No. 17/407,398, filed on Aug. 20, 2021, now Pat. No. 11,943,855, which is a continuation of application No. 16/864,860, filed on May 1, 2020, now Pat. No. 11,109,467.

(60) Provisional application No. 62/842,812, filed on May 3, 2019, provisional application No. 62/991,919, filed on Mar. 19, 2020.

(51) Int. Cl.
*H05B 47/16*   (2020.01)
*A61M 21/00*   (2006.01)
*A61M 21/02*   (2006.01)

(52) U.S. Cl.
CPC .............. *H05B 47/16* (2020.01); *A61M 21/02* (2013.01); *A61M 2021/0044* (2013.01)

(58) Field of Classification Search
CPC ........ H05B 47/16; H05B 45/20; A61M 21/02; A61M 2021/0044; A61M 2230/62; A61M 21/00; A61N 5/0618; F21S 10/00
See application file for complete search history.

(56) References Cited

U.S. PATENT DOCUMENTS

| | | | |
|---|---|---|---|
| 11,109,467 B2 | 8/2021 | Heller | |
| 11,943,855 B2 * | 3/2024 | Heller | H05B 47/16 |
| 2013/0085609 A1 | 4/2013 | Barker | |
| 2013/0119891 A1 * | 5/2013 | Herremans | H05B 47/16 |
| | | | 315/293 |
| 2015/0126806 A1 * | 5/2015 | Barroso | H05B 47/11 |
| | | | 315/153 |

(Continued)

FOREIGN PATENT DOCUMENTS

| | | |
|---|---|---|
| WO | WO 2014/053948 | 4/2014 |
| WO | WO 2014/115053 | 7/2014 |
| WO | WO 2020/227115 | 11/2020 |

OTHER PUBLICATIONS

International Search Report of related PCT/US2020/031078, mailed Aug. 4, 2020, 12 pages.

(Continued)

*Primary Examiner* — Renan Luque
(74) *Attorney, Agent, or Firm* — Casimir Jones, S.C.; David A. Casimir

(57) ABSTRACT

Provided herein are lighting devices, systems, and methods. In particular, provided herein are lighting systems configured for use in a variety of medical settings to improve patient and health care worker health, performance, and well-being.

7 Claims, 3 Drawing Sheets

TOP VIEW

(56) References Cited

U.S. PATENT DOCUMENTS

2018/0153012 A1    5/2018  Lee et al.
2020/0260543 A1    8/2020  Larson et al.
2020/0367341 A1   11/2020  Van Der

OTHER PUBLICATIONS

Leung et al., "Factors contributing to officers' fatigue in high-speed maritime craft operations" Appl Ergon. Sep. 2006;37(5):565-76.
Dijk et al., "Timing and consolidation of human sleep, wakefulness, and performance by a symphony of oscillators" J Biol Rhythms. Aug. 2005;20(4):279-90.
Lucas et al., "Measuring and using light in the melanopsin age" Trends Neurosci. Jan. 2014; 37(1): 1-9.
HHS "Adverse Events in Skilled Nursing Facilities: National Incidence Among Medicare Beneficiaries" Feb. 27, 2014 | Report (OEI-06-11-00370), 69 pages.
Solid State Lighting Program (Street lighting and Blue Light) (2017).
Stakeholder Meeting; Solutions based Lighting Year (2019).
Extended European Search Report for EP 20801643.6, mailed Jan. 5, 2023, 9 pages.

\* cited by examiner

Dining Room Specifications

◇ Recessed Can Lights (can also be recessed luminaires or other form factors)

- All M/P of > .85

Hallway Specifications

☐ 2x4 troffer fixture (can also be recessed luminaires or other form factors)

- Daytime M/P of > .85
- Nighttime M/P of < .35

Nurse's Station Specifications

2x2 troffer fixture (can also be recessed luminaires or other form factors)

- M/P .85 to 1.0, 24/7

TOP VIEW

Nurse's Station Specifcations (cont.)

BACK VIEW

- Task lights are connected to adjustable swivel
- M/P 1.0 or greater

SIDE VIEW

Resident Room Specs

A: Warm < .35 M/P, as desired

B: Warm < .35 M/P Evening/Night
Blue > .90 M/P Day

C: Warm < .35 M/P, as desired

D: Warm < .35 M/P, as desired

LIGHTING SYSTEMS AND APPLICATIONS THEREOF

This application is a continuation of U.S. patent application Ser. No. 17/407,398, filed Aug. 20, 2021, now U.S. Pat. No. 11,943,855, issued Mar. 26, 2024, which is a continuation of U.S. patent application Ser. No. 16/864,860, filed May 1, 2020, now U.S. Pat. No. 11,109,467, issued Aug. 31, 2021, which claims the benefit of U.S. Provisional Application No. 62/842,812, filed May 3, 2019, and U.S. Provisional Application No. 62/991,919, filed Mar. 19, 2020, the contents of which are hereby incorporated by reference in their entireties.

FIELD

Provided herein are lighting devices, systems, and methods. In particular, provided herein are lighting systems configured for use in a variety of medical settings to improve patient and health care worker health, performance, and well-being; assisted living facilities to improve resident health, performance and well-being; and correctional institutes to improve the incarcerated person's health, performance, and well-being.

BACKGROUND

Light, in the form of fire, was first harnessed by mankind 125,000 years ago. It slowly advanced through stages of fire for light until 1800, when Humphry Davy invented the first arc lamp based on electrical current from batteries. Then in 1879, Thomas Edison and Joseph Swan patented the first carbon thread incandescent lamp. Since that first patent by Edison, man-made lighting has advanced through fluorescents, high pressure sodium and now the LED revolution. All of these advances were based on more lumens/watt or better light solely for visual tasks. Vision is enabled by two photoreceptors, the rods and cones. In 1999 Samar Hattar discovered a third photoreceptor, the ipRGC. This is a non-visual photoceptor in mammals responsible for entraining the circadian clock, influencing mood, learning, vision, and potentially a host of yet undiscovered functions.

The manmade lighting environment includes, for example, healthcare facilities, nursing homes, assisted living facilities, correctional institutions, mental or psychological or mental facilities, schools and universities.

A skilled nursing facility provides specialized care and rehabilitation services to patients following a hospital stay. There are more than 15,000 skilled nursing facilities nationwide, and about 90 percent of them are also certified as nursing homes, which provide longer-term care. About 40 percent of people over age 65 will spend time in a nursing home at some point.

As hospitals have moved to shorten patient stays, skilled nursing care has grown dramatically. Medicare spending on skilled nursing facilities more than doubled to $26 billion between 2000 and 2010. About one-in-five Medicare patients who were hospitalized in 2011 spent time in a skilled nursing facility.

One-in-three patients in skilled nursing facilities suffered a medication error, infection or some other type of harm related to their treatment, according to a 2014 report by the U.S. Department of Health and Human Services (HHS) (February 2014; OEI-06-11-00370). Skilled nursing care is defined as treatment in nursing homes for up to 35 days after a patient was discharged from an acute care hospital. Doctors who reviewed the patients' records determined that 59 percent of the errors and injuries were preventable. More than half of those harmed had to be readmitted to the hospital at an estimated cost of $208 million for the month studied, about 2 percent of Medicare's total inpatient spending. The doctors found that 22 percent of patients suffered events that caused lasting harm, and another 11 percent were temporarily harmed. In 1.5 percent of cases the patient died because of poor care, the report said. Though many who died had multiple illnesses, they had been expected to survive.

The injuries and deaths were caused by substandard treatment, inadequate monitoring, delays or the failure to provide needed care, the study found. The deaths involved problems such as preventable blood clots, fluid imbalances, excessive bleeding from blood-thinning medications and kidney failure.

Fatigue of care providers, such as nurses or doctors is a factor in nursing homes and other facilities and can contribute to errors. Workload, work hours, work structures, and many other factors can indirectly or directly cause fatigue in multiple industries and affect safety.

Within the healthcare setting one of today's greatest challenges is delivering safer care in complex, fast-moving environments. Adverse events occur, and unintentional but serious harm comes to patients during routine clinical practice or as a result of a clinical decision. Fatigue is a factor that has been linked to stress, safety, and performance decrements in numerous work environments (Leung, Chan, Ng, & Wong, Applied Ergonomics, 37 (5), 565-576 2006).

Furthermore, many patient environments within healthcare facilities are one-size-fits all. These present non-ideal healing and recovery environments for many patients.

Additional methods for reducing errors and improving patient and staff well-being are needed.

SUMMARY

Provided herein are lighting devices, systems, and methods. In particular, provided herein are lighting systems configured, for example, for use in a variety of medical settings to improve patient and health care worker health, performance, and well-being.

During the past three decades, empirical evidence has demonstrated that many aspects of human physiology and behavior are influenced by retinal illumination (Aschoff, J. Handbook of behavioral neurobiology No. 4: Biological rhythms. New York: Plenum; 1981; Wurtman, R J.; Baum, M J.; Potts, J. The Medical and Biological Effects of Light. New York: The New York Academy of Sciences; 1985; Wetterberg, L. Light and Biological Rhythms in Man. Stockholm: Pergamon Press; 1993; Lam, R W. Beyond seasonal affective disorder: Light treatment for SAD and non-SAD disorders. Washington, D.C.: American Psychiatric Press, Inc; 1996). Such responses originate in the eye but are separate from other aspects of vision insofar as they are unrelated to particular spatial patterns of light exposure and can survive even in some blind subjects. Consequently, these types of light responses have been commonly referred to as non-image-forming or non-visual.

These catch-all terms encompass a wide array of response types. The most influential is light-induced phase resetting of endogenous circadian clocks. Because circadian rhythmicity is a feature of nearly every physiological, metabolic and behavioral system, this phenomenon brings a wide array of biological processes under indirect retinal control. Beyond this, the term non-visual response has come to encompass a growing list of more acute effects of light that together ensure a day-like physiological state. Thus, for example, light constricts the pupil, suppresses pineal melatonin production, increases heart rate and core body temperature, stimulates cortisol production, and acts as a neurophysiological stimulant (increasing subjective and objective measures of alertness and psychomotor reaction time, and reducing lapses of attention).

Appreciation of this basic biology has led to development of a number of therapeutic applications. Light has been shown to have anti-depressant properties, particularly in the treatment of seasonal affective disorder (SAD) and its subclinical variant, sSAD (Wetterberg, L. Light and Biological Rhythms in Man. Stockholm: Pergamon Press; 1993; Lam, R W. Beyond seasonal affective disorder: Light treatment for SAD and non-SAD disorders. Washington, D.C.: American Psychiatric Press, Inc; 1996). Appropriately timed light exposure has been developed as therapy for circadian rhythm sleep disorders and circadian disruption associated with jetlag, shift work and space flight.

Light has been explored as a treatment for non-seasonal depression, menstrual-cycle-related problems, bulimia nervosa, and cognitive and fatigue problems associated with senile dementia, chemotherapy and traumatic brain injury (Wetterberg, L. Light and Biological Rhythms in Man. Stockholm: Pergamon Press; 1993; Lam, R W. Beyond seasonal affective disorder: Light treatment for SAD and non-SAD disorders. Washington, D.C.: American Psychiatric Press, Inc; 1996; Tuunainen A, Kripke D F, Endo T. Light therapy for non-seasonal depression. The Cochrane Database of Systemic Reviews. 2004; 2:1-83; Human circadian rhythms: Regulation and impact. Journal of Biological Rhythms. 2005; 20 (4): 279-386).

These effects of light on physiology and behavior evolved over millennia in which environmental illumination provided a reliable indicator of time of day. The advent of manmade lighting has unintentionally disrupted this relationship, with patterns of light exposure now also reflecting personal tastes and social pressures, without an understanding of the significant impact on human physiology.

By optimizing the intensity, wavelength, and timings of lighting in facilities (e.g., medical facilities, assisted living facilities, prisons, etc.), the systems and methods described herein improve patient outcome by optimizing lighting for patient and staff alertness and sleep patterns.

For example, in some embodiments, provided herein is a lighting system for use in a facility (medical facility, including, but not limited to hospitals, clinics, assisted living facilities, nursing homes, prisons, and the like), comprising, consisting essentially of, or consisting of: a) a first lighting zone comprising a plurality of lighting components; b) a second lighting zone comprising a plurality of lighting components; and c) a controller configured to control the intensity, time, and wavelength of the first and second lighting zones. The present disclosure is not limited to particular first and second patient care zones. For example, in some embodiments, the first lighting zone is a patient care zone (e.g., patient room, ICU, etc.) and the second lighting zone is a non-patient care zone (e.g., a hallway and/or staff area). In some embodiments, one or more third lighting zones are provided. In some embodiments, the controller comprises a computer processor and computer software and optionally a user interface (e.g., one or more of a computer monitor, a keyboard, a voice activated device, a tablet, a smart phone, or a smart watch, including voice activated devices). In some embodiments, the lighting components comprise tunable and/or non-tunable light sources. Exemplary light sources are described below.

The present disclosure is not limited to particular lighting components and protocols for the first lighting zone. In some embodiments, the first lighting zone comprises a plurality of lights over a patient bed (e.g., a plurality of uplights, lights that project horizontal lights, and/or downlights), and a plurality of additional room lights. In some embodiments, the first lighting zone further comprises a plurality of bathroom lights. In some embodiments, the uplight has a melanopic/photopic (M/P) ratio of 0.7 to 1.2 (e.g., 0.75 to 0.95, 0.8 to 1.0, or 0.85 to 1.1) plus or minus no more than 0.1%, 0.5%, 1.0%, 5%, 10%, or 20% and the downlight has an M/P ratio of 0.2 to 0.5 (e.g., 0.2 to 0.4, 0.2 to 0.35, 0.3 to 0.45, 0.3 to 0.4, or 0.35) plus or minus no more than 0.1%, 0.5%, 1.0%, 5%, 10%, or 20%. In some embodiments, the plurality of room lights have an M/P ratio of less than 0.2 to 0.5 (e.g., 0.2 to 0.4, 0.2 to 0.35, 0.3 to 0.45, 0.3 to 0.4, or 0.35) plus or minus no more than 0.1%, 0.5%, 1.0%, 5%, 10%, or 20%. In some embodiments, room lights are matched to hallway lights, or adjust automatically based on the time of day. In some embodiments, the bathroom lights have an M/P ratio of less than 0.2 to 0.5 (e.g., 0.2 to 0.4, 0.2 to 0.35, 0.3 to 0.45, 0.3 to 0.4, or 0.35) at night and 0.7-1.2 (e.g., 0.7 to 1.0, 0.7 to 0.8, 0.8 to 1.2, 0.8 to 1.0, 0.8 to 0.9, 0.9 to 1.2, 0.9 to 1.1, 0.9 to 1.0, or 1.0 to 1.2) during the day, both plus or minus no more than 0.1%, 0.5%, 1.0%, 5%, 10%, or 20%. In some embodiments, the room lights are one or more of can lights, ceiling lights, floor lamps, or similar fixtures. In some embodiments, the first lighting zone is configured to turn on the uplight in the morning or other preselected time where a waking state is desired and turn off the uplight in the evening or some other time where a sleeping state or transition to sleeping state is desired. In some embodiments, the uplight has an illuminance of 50 to 150 lux (e.g., 50 to 100, 75 to 150, 100 to 150, or 100 lux) plus or minus no more than 0.1%, 0.5%, 1.0%, 5%, 10%, or 20% as measured on a vertical plane near the eye of a patient in the bed. In some embodiments, the position and/or intensity of the light is altered to provide the desired illumination properties in response to the patient position. For example, in some embodiments, one or more sensors in the room monitors the head or eye position of the patient and the system modulates light position or intensity to maintain the desired illumination received by the patient. In some embodiments, the system is configured to turn all of the lights in the first zone off or to a desired luminescence at bedtime. In some embodiments, the first lighting zone further comprises a night light with a M/P ratio of less than 0.5 (e.g., 0.5, 0.45, 0.4, 0.35, 0.3, 0.25, or 0.2) plus or minus no more than 0.1%, 0.5%, 1.0%, 5%, 10%, or 20%, wherein the night light remains on during sleeping hours. In some embodiments, the system monitors ambient light in the zone and adjusts artificial light to achieve the desired illumination of the patient. Thus, different patient zones may receive different lighting protocols dependent on the presence or amount of ambient light (e.g., a room with windows to the outside will utilize a different protocol than a room without windows). Likewise, within a single zone, two or more locations in the zone may utilize different protocols. For example, a room with two patients may use a first protocol for lighting near a first patient near a window and a second protocol for lighting near a second patient away from the window. The lighting protocol may also be altered in real-time in response to changes in ambient lighting, for example, due to changes in weather, cloud cover, the opening and closing of blinds, or the introduction of barriers (e.g., curtains, medical equipment, etc.) between a window and a subject.

The present disclosure is not limited to particular lighting components and protocol for a second zone (e.g., hallway area, staff room, etc.). For example, in some embodiments, the hallway lights have a M/P ration of 0.7 to 1.2 (e.g., 0.75 to 0.95, 0.8 to 1.0, or 0.85 to 1.1) plus or minus no more than 0.1%, 0.5%, 1.0%, 5%, 10%, or 20% during the day and 0.2 to 0.5 (e.g., 0.2 to 0.4, 0.2 to 0.35, 0.3 to 0.45, 0.3 to 0.4, or 0.35) plus or minus no more than 0.1%, 0.5%, 1.0%, 5%, 10%, or 20% in the evening and night. In some embodiments, the system is configured to turn the hallway lights on to 150 to 350 lux (e.g., 150 to 300, 150 to 250, 200 to 350, 200 to 300, or 200 lux) plus or minus no more than 0.1%, 0.5%, 1.0%, 5%, 10%, or 20% in the early morning, 350 to 550 lux (e.g., 350 to 500, 350 to 450, 400 to 550, 400 to 500, or 400 lux) plus or minus no more than 0.1%, 0.5%, 1.0%, 5%, 10%, or 20% mid morning, 150 to 350 lux (e.g., 150 to 300, 150 to 250, 200 to 350, 200 to 300, or 200 lux) plus or minus no more than 0.1%, 0.5%, 1.0%, 5%, 10%, or 20% in the mid afternoon, 200 to 400 (e.g., 200 to 350, 200 to 300, 250 to 400, 250 to 350, or 300 lux) plus or minus no more than 0.1%, 0.5%, 1.0%, 5%, 10%, or 20% in the evening, and 50 to 250 (e.g., 50 to 200, 100 to 250, 100 to 200, or 150 lux) plus or minus no more than 0.1%, 0.5%, 1.0%, 5%, 10%, or 20% at bed time. In some embodiments, the lux values are measured on a vertical plane near the eye of an individual (e.g., standing, sitting or other position). In some embodiments, the M/P ratio of lights in said first zone matches the M/P ratios of light in said the second zone during the day and evening.

The present disclosure is not limited to particular lighting components and protocol for a staff area. For example, in some embodiments, the staff area comprises light with a M/P ratio of greater than 0.7 to 1.2 (e.g., 0.75 to 0.95, 0.8 to 1.0, or 0.85 to 1.1) plus or minus no more than 0.1%, 0.5%, 1.0%, 5%, 10%, or 20%. In some embodiments, the staff area comprises one or more areas selected from a nurse's station, guard area, correctional officer area, and/or a staff break room. In some embodiments, the staff lighting is at a level of at least 50 to 150 lux (e.g., 50 to 100, 75 to 150, 100 to 150, or 100 lux) plus or minus no more than 0.1%, 0.5%, 1.0%, 5%, 10%, or 20% measured on a vertical plane from the eyes. In some embodiments, light from staff areas is not visible in the patient rooms.

The present disclosure is not limited to a particular facility. Examples include, but are not limited to, a skilled nursing facility, an assisted living facility, a hospital, a hospice, a clinic, an outpatient surgery center, a temporary or portable medical facility (e.g., tent, truck, plane, etc.), a prison, or a jail.

Additional embodiments provide a method of controlling lighting in a facility, comprising: operating a system as described herein in a facility. In some embodiments, the system is operated manually, is automated, or a combination thereof. In some embodiments, the system automatically adjusts the timing, intensity, or wavelength of the lights based on one or more of sunrise, sunset, or predetermined time.

Yet other embodiments, provided herein are methods of improving outcomes (e.g., of speed of healing, reducing medical errors, increasing staff alertness, reducing falls of patients, reducing sundowners, and/or reducing the need for or amount of medication (e.g., psychotropic medication) for patients in a facility: operating a system as described herein. Additional embodiments are described herein.

DETAILED DESCRIPTION

Figure 1:
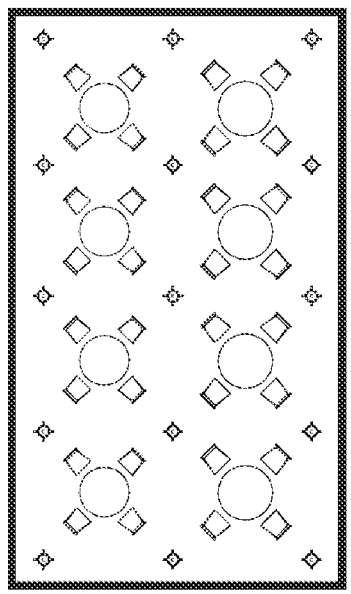
FIG. 1 shows exemplary layout and specifications of dining room lighting.

Provided herein are lighting devices, systems, and methods. In particular, provided herein are lighting systems configured for use in a variety of medical settings to improve patient and health care worker health, performance, and well-being.

The lighting systems described herein are customizable, programmable, and adaptable. The lighting systems provide optimum timing, intensity, and spectrum for each location. In some embodiments, such as a medical setting, individual lighting settings are utilized for specific patients or zones containing certain types of patients to provide optimized lighting for a specific category of patient (e.g., based on disease or condition type, age, stage of healing, etc.). In some embodiments, specific times of day and/or locations utilize specific protocols based on historic incidents of fatigue-related problems or injuries.

In some embodiments, the optimization of lighting results in one or more positive outcomes, for example, improving and speed of healing, reducing medical errors, increasing staff alertness, reducing falls, reducing sundowners, and reducing the need for psychotropic medication.

The biological and behavioral effects of light are influenced by a distinct photoreceptor in the eye, melanopsin containing intrinsically photosensitive retinal ganglion cells (ipRGCs), in addition to the conventional rods and cones (See e.g., Lucas et al., Trends Neurosci. 2014 January; 37 (1): 1-9). Accordingly, in certain embodiments, light spectrum is measured using the melanopic/photopic (M/P) ratio. The M/P ratio does not describe color but rather how much blue content (light at 480 nm) is in the light.

The M/P ratio is measured at eye level facing the direction the occupant would normally face when completing their tasks during a typical day. A calibrated spectrometer is utilized to measure the light spectrum in u W/cm$^2$/nm (micro watts/centimeter squared/nanometer) at typical eye levels. This data is then collected and analyzed to determine the 5 measurement output values, corresponding to the human retinal photoreceptor complement. The photoreceptor complement includes Cyanopic, Melanopic, Rhodopic, Chloropic, and Erythropic values. Upon determining the u W/cm$^2$/nm for the melanopic value, it is compared to the photopic value yielding an M/P ratio. An M/P ratio above. 9 is a light source that will suppress melatonin and increase alertness.

In some embodiments, the M/P ratio is altered in different locations in a facility in order to optimize patient and staff performance and well-being. For example, in some embodiments, patient rooms are provided with light with lower M/P ratios in the evening in order to promote relaxation and decrease alertness of patients. In some embodiments, the M/P ratio is increased during the day to increase alertness. In general, staff areas such as a nurse's station, hallways, break rooms, and medical procedure rooms (e.g., operating rooms) are kept at a higher M/P ratio at all times to increase staff alertness. In the present disclosure, M/P ratios of lights used in the described systems range from 0.2 to 1.2 (e.g., 0.2, 0.25, 0.3, 0.35, 0.4, 0.45, 0.5, 0.55, 0.60, 0.65, 0.70, 0.75, 0.80, 0.85, 0.9, 0.95, 1.0, 1.2 or fractions thereof) plus or minus no more than 0.1%, 0.5%, 1.0%, 5%, 10%, or 20%, depending on the time of day or subject population. Exemplary lighting protocols for different areas of a facility are provided below.

In some embodiments, lights are "tunable." For example, as used herein a "tunable" light source is a light source (e.g., light emitting diode or other light source or lamp) configured to be tuned to alternative wavelengths of light (e.g., using a controller). Examples of light source suitable for use in the present disclosure include, but are not limited to, light sources with a plurality of LEDs of different wavelengths that can be turned on and off via a controller, broad spectrum lights (e.g., DC arc lamps) with filters or diffraction gratings to tune the wavelength of light emitted, and the like. In some embodiments, tunable commercial lights sources available from a large number of suppliers (e.g., Acuity Brands (Atlanta, GA); Lighting Science (West Warwick, RI) and Elite Lighting (Los Angeles, CA) are utilized in the present disclosure.

In some embodiments, light sources comprise dimmers to adjust the intensity of the light (e.g., measured in lux). The lux is the International System of Units derived unit of illuminance and luminous emittance, measuring luminous flux per unit area. In some embodiments, lux values are lux values at the eye level regardless of the individual's position. In some embodiments, the height is the average height of an individual present in the particular region of the facility receiving the light. In some embodiments, the height is the actual height of the individual, as measured by a sensor or pre-programmed based on a known height of the individual.

In some embodiments, lighting systems comprise a controller (e.g., comprising a computer processor, computer software, and optionally a user interface such as for example, a computer monitor, a tablet, a smart phone, or smart watch). The controller serves to control all or a portion of the lights in the system. In some embodiments, lights are wired via electrical wires to the system. In other embodiments, lights are controlled wirelessly (e.g., via Bluetooth, near field, WiFi, or a combination thereof). Various different configurations (e.g., a combination of wired and wireless interfaces) are envisioned by the present disclosure.

In some embodiments, the controller is programmed to automatically adjust lighting based on the region of the facility or time of day. In some embodiments, a user manually controls the lighting. In some embodiments, the user interface (e.g., voice, touch, or keypad interface) allows a user to alter the automated protocol. In some embodiments, a plurality of protocols is stored in memory and are selected by a user interface. Such protocols include zone-specific protocols, patient specific protocols (based on patient categories such as health status, age, and the like), room specific protocols, and the like. In some embodiments, the processor is located at a site remote from the facility or on-site. For example, in some embodiments, a service provider manages the lighting systems of two or more different facilities remotely. In some embodiments, patient and staff outcome data is collected from one or more such facilities to allow further optimization based on tracked outcomes (e.g., across a large number of facilities using data pooled from the facilities). In some embodiments, experimental protocols are run to identify improved protocols.

In some embodiments, a facility is divided into zones with different lighting needs. For example, in some embodiments, facilities comprise first, second, and optionally third (or more) zones. In some embodiments, within a zone, lighting is uniform (e.g., all lights of a given type within a zone are set to the same M/P ratios and lux values), although each zone may include different types of lighting components that vary from other types of lighting components. For example, in a zone comprising a patient room, all of the bed lights in the zone are set to the same parameters bed overhead lights in the rooms are set to different parameters.

The present disclosure is not limited to particular lighting zones. In some embodiments, lighting systems comprise a first zone comprising patient care zones (e.g., patient bedrooms, patient apartments, or common areas). In some embodiments, lighting systems comprise a second zone comprising staff areas (e.g., one or more of nurse's station, hallways, staff rooms, or medical procedure rooms). A facility may have any number of different zones depending on the needs of a given facility (e.g., 1, 2, 3, 4, 5, or more zones per facility).

The present disclosure is not limited to particular facilities. Examples include, but are not limited to, skilled nursing facilities, long term care facilities, hospitals, hospices, assisted living facilities, clinics, correctional facilities (e.g., prisons, jails, youth facilities, etc.) and outpatient surgery centers.

By way of example, the below description provides exemplary zones and lighting protocols illustrated for a skilled nursing home or long-term care facility. The description is for illustrative purposes and does not limit the disclosure.

Figure 2:
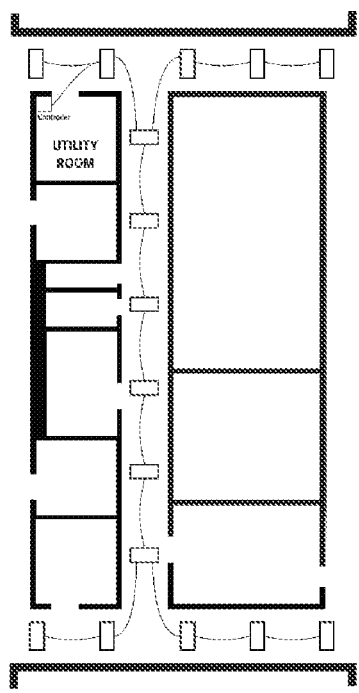
FIG. 2 shows exemplary layout and specifications of hallway lighting.
Figure 3A:
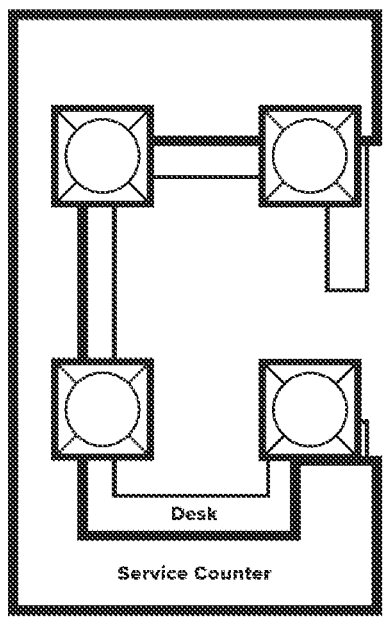
FIG. 3 shows a) a top view and b) side view of exemplary layout and specifications of nursing station lighting.
Figure 3A:
Figure 3A:
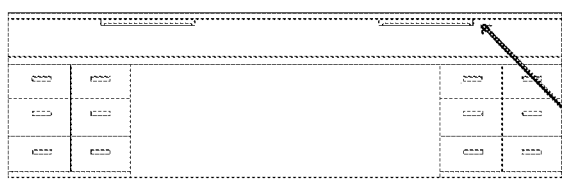
Figure 3B:
Figure 4:
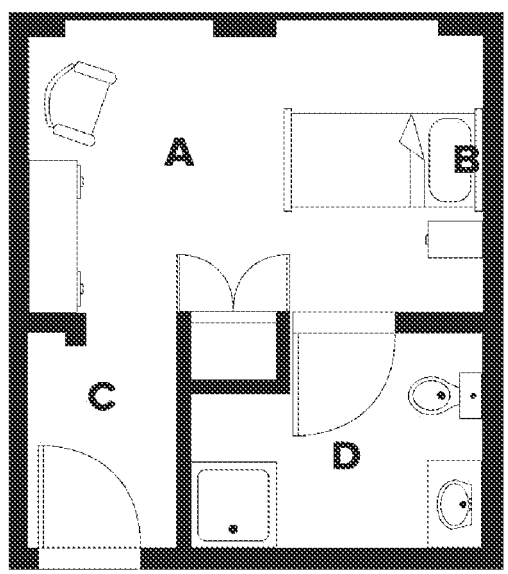
FIG. 4 shows exemplary layout and specifications of resident room lighting.

FIGS. 1-4 show exemplary layouts and specifications of certain rooms described below. FIG. 1 shows a layout of a dining room ceiling lighting with an M/P of greater than 0.85. FIG. 2 shows a layout of a hallway ceiling lighting with a daytime M/P of greater than 0.85 and a nighttime M/P of less than 0.35. FIG. 3 shows a) top and b) side views of a nurse's station with ceiling lighting of an M/P of 0.85 to 1.0 and task lighting of an M/P of 1.0 or greater. FIG. 4 shows a ceiling view of a resident or patient room with ceiling lights A with an M/P of less than 0.35, bed lighting B configured for an M/P of less than 0.35 during evening and night hours and an M/P of greater than 0.9 during the day, entry lighting C with M/P of less than 0.35, and bathroom lighting D with an M/P of less than 0.35. In some embodiments, lights change color (e.g., M/P ratio) automatically based on the time of day.

Patient Room Lights

Patient room lighting is enhanced throughout the 24 hour day to improve overall patient health and wellbeing. This results in, for example, reduction of falls, improved healing after illness or medical procedures, and a reduction in medications. In some exemplary embodiments, patient rooms comprise over the bed lights with 2 light sources, an uplight with a minimum M/P ratio of 0.9 and a down light with a maximum M/P ratio of 0.35. In some embodiments, any other resident lights, can lights, ceiling lights, floor lamps have an M/P ratio of 0.35 or below. In some embodiments, bathrooms comprise light with an M/P ratio of less than 0.5 at night and 0.9 during the day.

In some embodiments, patient room lights utilize the following protocol: In the morning (e.g., between 6 and 7 AM), the uplight is energized or turned on to start the resident's day. It immediately suppresses melatonin production and encourages cortisol production. This hormone makes the resident more alert and energetic and sets the resident's internal body clock or circadian rhythm. Every cell in the body has a clock and the signal from the photons at a minimum of 0.9 M/P ratio entering the pupil will send a signal to the cells that daytime has started and it is time to start their daytime mode. In some embodiments, the illuminance is 100 lux as measured on a vertical plane near the eye. At the evening meal time (e.g., between 5 and 6 PM), the uplight is turned off to signal the beginning of the night time mode. All the other low M/P (below 0.35) lights remain on all day and into the evening. At bedtime, all lights are turned off and measurable light should be 0 lux. If there is a night light, it should have an M/P ratio below 0.35 and should be directed at the floor. In general, the lighting in the resident rooms should match the color of the light in the hallway during daytime and evening hours.

Hallway Lights

Hallway lighting is optimized to the time of day, as many different individuals are exposed to the hallway lights. In some exemplary embodiments, in the morning (e.g., between 6 and 7 am), the hallway lights are turned up to 200 lux as measured on a vertical plane near the eye with an M/P ratio of at least 0.9. In some embodiments, at mid-morning (e.g., 10 AM) the hallway lights are increased to 400 lux* measured on a vertical plane near the eye. In some embodiments, mid-afternoon (e.g., 3 PM) illuminance is lowered to 200 lux* measured on a vertical plane near the eye. In some embodiments, at the time of the evening meal (e.g., between 5 and 6 PM), the M/P ratio is lowered to below 0.35 M/P with in an illuminance of 300 lux* as measured on a vertical plane near the eye. At bedtime (e.g. 9:00 PM), the illuminance is 150 lux* as measured on a vertical plane near the eye.

Activity Areas

In some embodiments, lights in activity areas (e.g., craft areas, game areas, social areas, etc.) are kept at a high M/P ratio at all times. In some embodiments, lights in activity areas are at 200 to 400 lux as measured on a vertical plane near the eye with an M/P ratio of at least 0.9 at all times they are in use.

Staff Lighting

The goal of enhancing lighting for staff locations is to reduce medical errors and accidents. In some exemplary embodiments staff areas (e.g., break rooms, nurse's stations, medical procedure rooms, etc.) provide rich blue light (e.g., M/P greater than 0.9). Exposing the staff to this light suppresses the production of melatonin and makes them more alert and energetic regardless of the shift they work. In some embodiments, the illuminance at the eye is a minimum of 100 lux as measured on a vertical plane near the eye. In some embodiments, patient areas are isolated from staff areas so that they are not exposed to the high M/P lights.

Using the described protocol, the following outcomes were observed: A reduction in the number of falls by 30%, a reduction in the number of sundowners by 35%, a reduction in the need for psychotropic meds by 10%, a reduction in harmful medical errors by 25%, and a reduction in energy consumption by 65%.

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A method of managing lighting in a health care facility with a centralized lighting control system, comprising:
    a) controlling lighting in a patient care zone that comprises a plurality of tunable and/or non-tunable lighting components comprising a plurality of uplights and downlights over a patient bed, and a plurality of additional room lights, wherein said downlights and said additional room lights deliver an melanopic/photopic (M/P) ratio of less than 0.5 as measured at an illuminance of 75 lux on a vertical plane at eye level, and said uplights deliver an M/P ratio greater than said downlights and said additional room lights as measured at an illuminance of 75 lux on a vertical plane at eye level;
    b) controlling lighting non-patient care zone that comprises a plurality of tunable and/or non-tunable lighting components; wherein said lighting in said non-patient care zone delivers a M/P ratio less than 0.5 in the evening and night at an illuminance of 75 lux on a vertical plane as measured at eye level; and
    c) controlling lighting in a staff zone that comprises a plurality of tunable and/or non-tunable lighting components; wherein said lighting in said staff zone delivers a M/P ratio of greater than 0.7 at an illuminance of 75 lux on a vertical plane as measured at eye level.

2. The method of claim 1, wherein the health care facility is selected from the group consisting of a skilled nursing facility, a long-term care facility, an assisted living facility, and a mental hospital facility.

3. The method of claim 1, wherein said patient care zone is a patient room.

4. The method of claim 1, wherein the lighting in the staff zone is non-tunable lighting.

5. The method of claim 1, wherein the patient care zone further comprises a plurality of bathroom lights that deliver a M/P ratio of less than 0.5 at night as measured at an illuminance of 75 lux on a vertical plane at eye level.

6. The method of claim 1, wherein said uplights are turned on at a preselected time when waking is desired and wherein said uplights are turned off at a pre-selected time where a sleeping state or transition to sleeping state is desired.

7. The method of claim 1, wherein said lighting components are adjusted to their intensity and/or spectrum automatically based on the time of day.

* * * * *